(12) United States Patent
Grey

(10) Patent No.: US 7,089,942 B1
(45) Date of Patent: Aug. 15, 2006

(54) ENDOTRACHAEL TUBE WITH SUCTION CATHETER AND SYSTEM

(76) Inventor: Christopher Grey, 11001 SW. 25th St., Davie, FL (US) 33324

(*) Notice: Subject to any disclaimer, the term of this patent is extended or adjusted under 35 U.S.C. 154(b) by 0 days.

(21) Appl. No.: 11/152,799

(22) Filed: Jun. 14, 2005

Related U.S. Application Data

(63) Continuation-in-part of application No. 10/768,580, filed on Jan. 30, 2004.

(60) Provisional application No. 60/445,629, filed on Feb. 7, 2003.

(51) Int. Cl.
*A61M 16/00* (2006.01)

(52) U.S. Cl. ............... 128/207.14; 128/207.15

(58) Field of Classification Search ........... 128/200.26, 128/207.14, 207.15, 207.16, 205.19, 206.11; 604/93.01, 95.03, 96.01, 103, 103.07; 606/108, 606/191, 192, 196

See application file for complete search history.

(56) References Cited

U.S. PATENT DOCUMENTS

| | | | |
|---|---|---|---|
| 4,156,428 A | 5/1979 | Henkin | |
| 4,305,392 A | 12/1981 | Chester | |
| 4,334,534 A | 6/1982 | Ozaki | |
| 4,584,998 A | 4/1986 | McGrail | |
| 4,607,635 A | 8/1986 | Heyden | |
| 4,632,108 A | 12/1986 | Geil | |
| 4,637,389 A | 1/1987 | Heyden | |
| 4,688,568 A | 8/1987 | Frass et al. | |
| 4,762,125 A | 8/1988 | Leiman et al. | |
| 4,840,173 A | 6/1989 | Porter, III | |
| 5,143,062 A | 9/1992 | Peckham | |
| 5,520,175 A | 5/1996 | Fry | |
| 6,062,223 A * | 5/2000 | Palazzo et al. ......... | 128/207.15 |
| 6,460,540 B1 * | 10/2002 | Klepper .................. | 128/207.14 |
| 6,796,309 B1 * | 9/2004 | Nash et al. ............. | 128/207.14 |
| 6,840,242 B1 * | 1/2005 | McCoy .................. | 128/207.14 |

* cited by examiner

*Primary Examiner*—Teena Mitchell
(74) *Attorney, Agent, or Firm*—David P. Lhota, Esq.; Stearns Weaver Miller Weissler Alhadeff & Sitterson, P.A.

(57) ABSTRACT

An endotracheal tube and suction catheter system having an inflatable cuff with a collection pocket formed in the cuff for collecting pooled secretions and a railing system for controllably guiding a suction catheter along the tube and into the pocket for aspirating pooled secretions. The cuff has an elongated parallelogram-like shape to counter the rocking phenomenon caused by a patient coughing or turning to keep the cuff in contact with the trachea wall so secretions do not leak past the cuff balloon. The railing system allows the suction catheter to be replaced without having to remove the endotracheal tube from the patient.

11 Claims, 8 Drawing Sheets

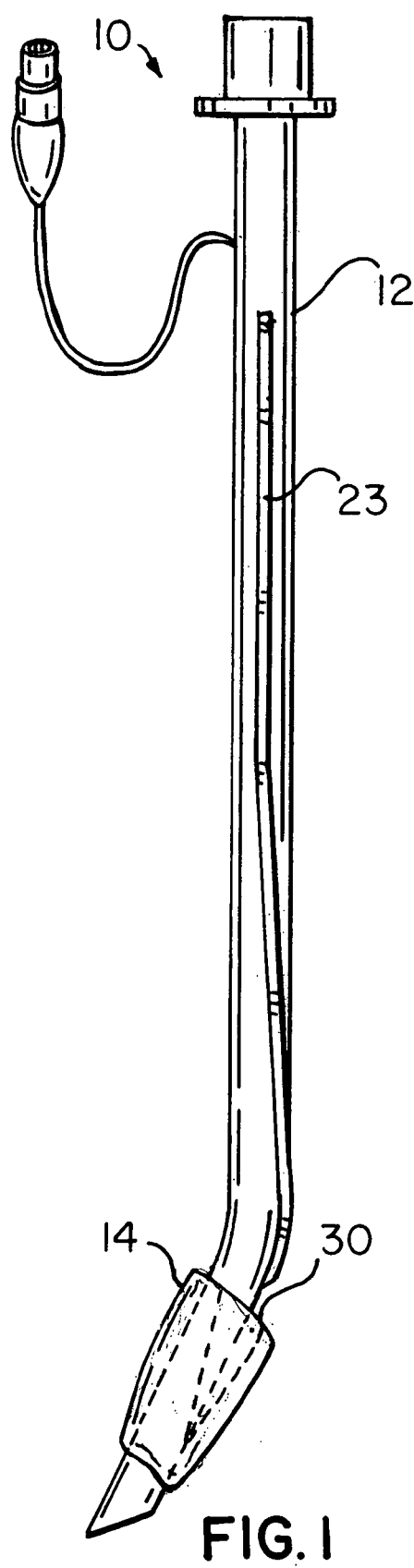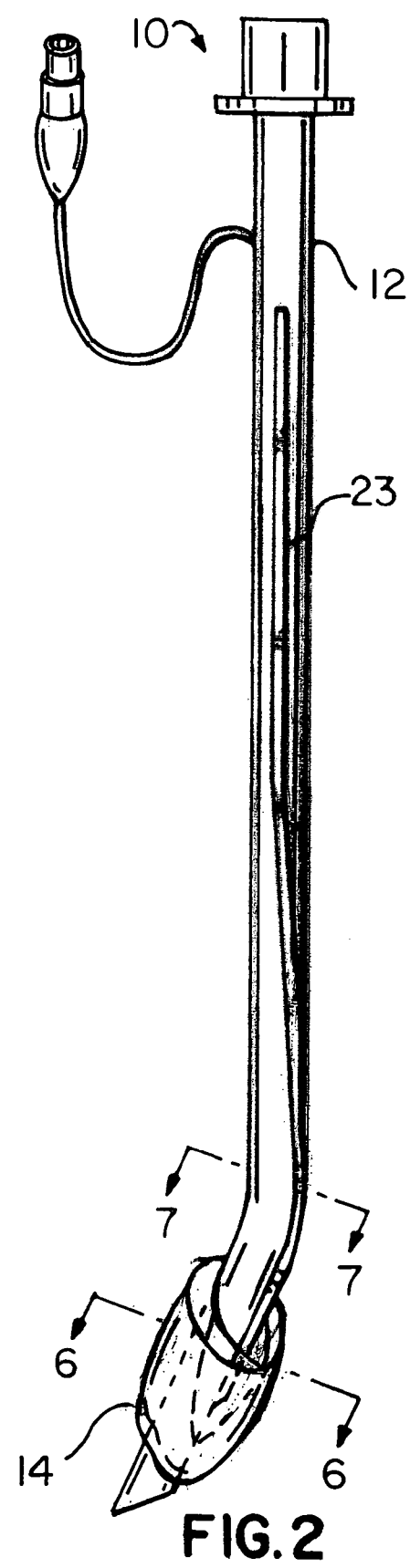

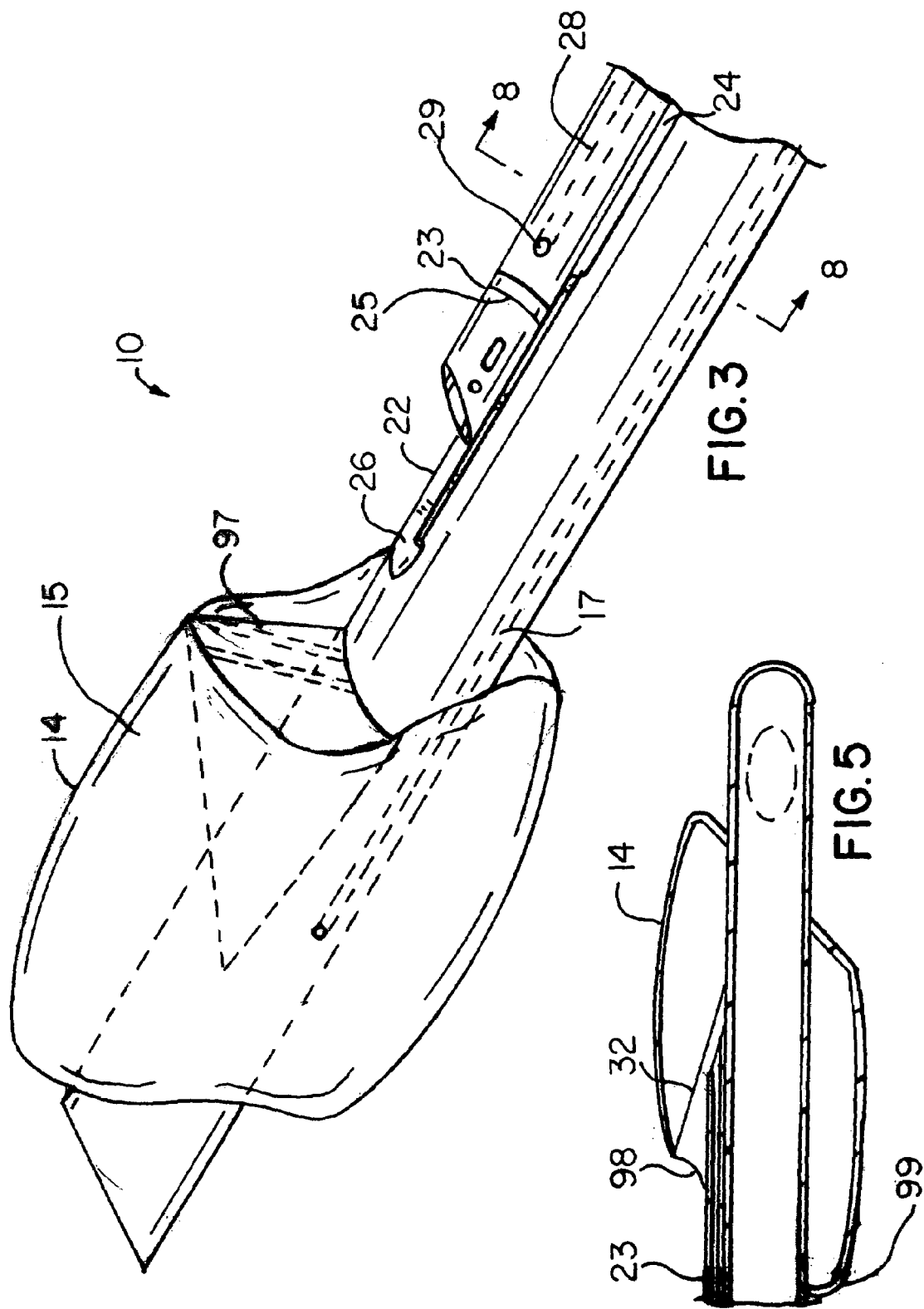

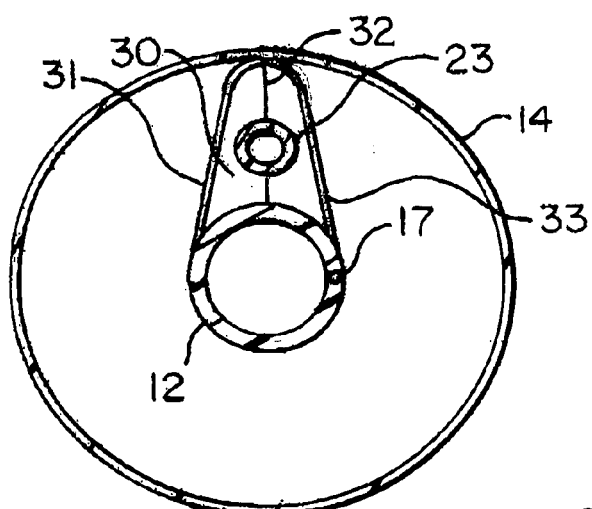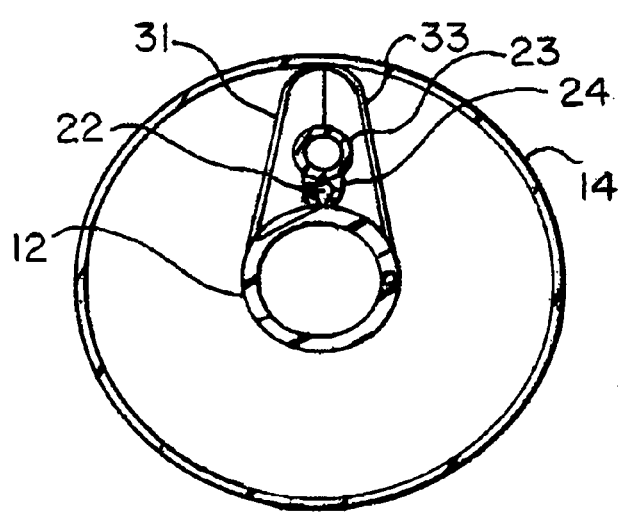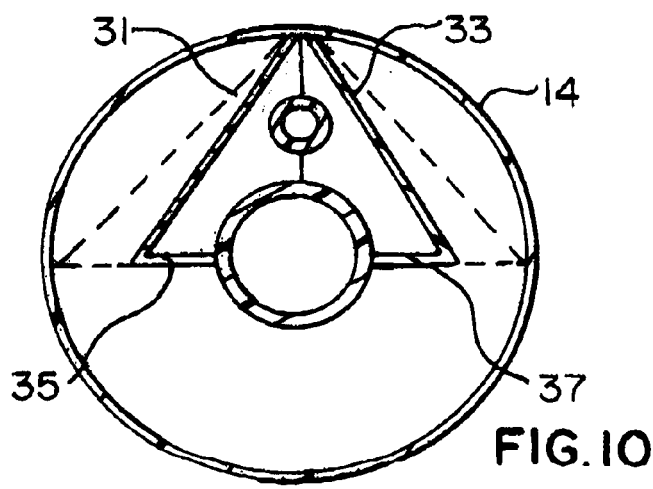

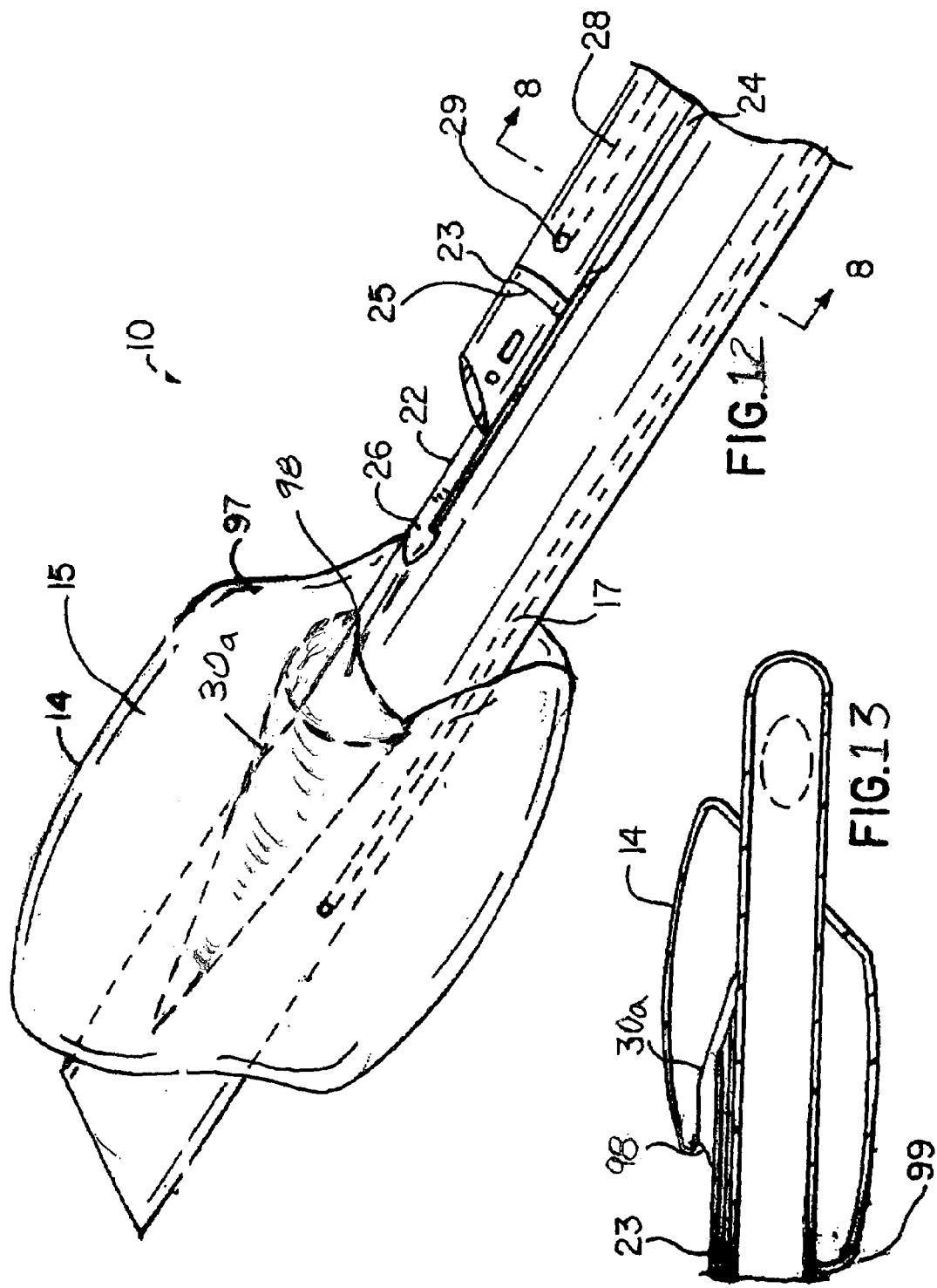

ENDOTRACHAEL TUBE WITH SUCTION CATHETER AND SYSTEM

CROSS REFERENCE TO RELATED APPLICATIONS

This application is a continuation-in-part of U.S. patent application Ser. No. 10/768,580, filed Jan. 30, 2004, which claims the benefit of U.S. Provisional Patent Application Ser. No. 60/445,629, filed Feb. 7, 2003.

STATEMENT REGARDING FEDERALLY SPONSORED RESEARCH OR DEVELOPMENT

N/A

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office patent file or records, but otherwise reserves all copyrights rights whatsoever.

BACKGROUND OF THE INVENTION

1. Field of the Invention

This invention generally relates to an endotracheal tube, and more particularly, to an endotracheal tube having an inflatable cuff that forms a tapered collection pocket when inflated for urging the collection of secretions and a rail system adapted for securely and safely guiding a suction catheter along the tube for facilitating the aspiration of secretions pooled in the cuff pocket and the area above the trachea.

2. Description of Related Art

A well known problem with endotracheal tubes is the buildup of excessive oropharyngeal and gastroesophageal secretions above the cuff of the tube in the trachea and subglottic area when a patient is intubated. Endotracheal intubation is used for mechanically ventilating a patient's lungs when the patient cannot breathe normally and/or for introducing anesthetic gases into the lungs. However, the intubated patient is almost always placed at risk by the accumulation of pooled secretions between the inflated cuff and oral pharyngeal area. The accumulation and stagnation of oral secretions breeds infectious organisms that can result in pneumonia. The accumulated secretions eventually leak into the patient's lungs or find their way into the lungs when the endotracheal cuff is deflated for removal or when a patient is turned and, or coughs. Conventional procedures for preventing pneumonia associated with tracheal intubation require confirmation that secretions are cleared from above the tube cuff before deflating the cuff and removing the tube. Some endotracheal tubes have a dorsal lumen formed in the walls of the tube above the cuff for draining accumulated secretions by suction. However, there are no known recommendations for routinely and effectively using an endotracheal tube with a dorsal lumen. This is in part due to the fact that the dorsal lumen can become easily occluded, which would require complete removal of the tube. Thus, intubated patients are always at risk of developing bronchitis, pneumonia and other life-threatening infections because of pooled secretions entering the trachea and lungs.

Up until 1936, pneumonia was the leading cause of death in the United States. Even with all the modern advances in medical technology and antibiotic therapy, pneumonia is currently the sixth leading cause of death in the U.S. (CDC, 1997). Nosocomial (hospital-acquired) pneumonia is a frequent complication in mechanically-assisted ventilator patients, according to a national, multi-million dollar, multi-center research study by the Centers for Disease Control (1997), pneumonia is the second most common nosocomial infection in the United States and is associated with substantial morbidity and mortality. The CDC further states that because intubation and mechanical ventilation alter first-line patient defenses, they greatly increase the risk for nosocomial bacterial pneumonia. The risk for pneumonia is increased by the direct access of bacteria to the lower respiratory tract, which often occurs because of leakage around the endotracheal cuff, thus enabling pooled secretions above the cuff to enter the trachea. According to Marino (1998), the aspiration of mouth secretions into the upper airways is the inciting event in most cases of pneumonia. An average of 1 billion bacteria are found in each milliliter of saliva, so aspirating only a micro-liters of saliva can introduce large numbers of bacteria into the airways.

According to Lewis et al (1997), endotracheal intubation interferes with the normal cough reflex and the mucociliary escalator mechanism. Decreased consciousness depresses the cough and epiglottal reflexes, which may allow aspiration of oropharyngeal contents into the lungs. It also bypasses the upper airways in which filtration and humidification of air normally take place (622).

Nosocomial pneumonia is a complication that not only increases mortality/morbidity rates, but also causes substantial increases in financial costs due to significant increases in length of stays (LOS) in high tech, intensive-care units. A one-two week increase in a patient's LOS in an ICU is a very significant fiscal consideration and hardship, which can cost $3,500.00 to $5,000.00 a day.

Conventional endotracheal tubes contribute to the problems associated with pooled secretions in the trachea area. The conventional endotracheal tube has an inflatable cuff that blocks the passageway and allows secretions to accumulate above the cuff. The tube has an inflation lumen that extends between a proximal end and a distal end for inflating the cuff. The inflatable cuff is joined to the tube above the distal end to prevent the passage of fluids and gases to and from the lungs when inflated. The cuff is inflated so that it engages the trachea wall thereby providing a proper seal. However, as the trachea is sealed, oral secretions tend to pool or build up above the cuff. If these secretions could be safely and conveniently aspirated the foregoing health concerns could be eliminated or greatly reduced. However, costs and practical constraints have prevented the adoption of a reliable, cost effective endotracheal and aspiration system.

In addition to the foregoing, conventional endotracheal tubes are limited in their use, difficult to monitor and provide methods of treatment but no information. As endotracheal tubes invade the body, it would be beneficial and helpful if it could provide useful information. For instance, if an endotracheal tube could be designed to also monitor a patient's temperature it would provide important medical information to a practitioner.

Moreover, an endotracheal tube that was able to provide a means for early detection of tissue hypoperfusion, such as structure for measuring oropharyngeal $PCO_2$, would provide an additional benefit over conventional tubes. An elevation in oropharyngeal $PCO_2$ is an early warning signal for tissue hypofusion. Limiting the risk of organ damage resulting from tissue hypoxia is one of the biggest challenges in patient care. Because tissue perfusion and oxygenation help maintain organ vitality, tissue perfusion is literally a matter of life and death. A noninvasive sublingual system known in the prior art and sold under the trademark CapnoProbe measures $PCO_2$ through fiber optic technology. Such devices comprise additional required equipment and can be expensive. An endotracheal tube having structure for continuously measuring oropharyngeal $PCO_2$ could provide a more economical device and more convenient option that facilitates taking continuous measurements and would be well received.

Endotracheal tubes are not new in the art and several have provided structure for draining fluid from the lungs and/or insufflating the lungs with oxygen or other gases. Other known devices have addressed the problem of removing pooled secretions through the cuff opening 98 from the upper tracheal area, but have failed to solve the problem as contemplated by the instant invention. Many of the endotracheal tubes known have a suction lumen that is integrally formed along or through the wall of the endotracheal tube. This design increases the thickness of the tube and calls for the entire endotracheal tube to be discarded when the suction lumen becomes damaged or permanently occluded or is the wrong size for the required aspiration. Designs that have a separate but permanently attached catheter can rupture the trachea wall. These endotracheal tubes and similar designs have edges that could scrape and cause trauma to the tracheal passageway.

The prior art devices known are disclosed in the following patents. U.S. Pat. No. 5,143,062, issued to Peckham, discloses an endotracheal tube comprising a double lumen through which air may be circulated, creating an indirect gentle suction through a suction eye communicating with the distal ends of the lumens, and located at a position proximal to the inflation cuff. This design, however, does not provide adequate suction necessary for aspirating secretions and is easily occluded. The Peckham device, is not practical for convenient hospital use and appears to be unsuitably thick. U.S. Pat. No. 4,305,392, issued to Chester, discloses an inflatable cuff type endotracheal tube having a suction chamber adjacent to the upper-side of the cuff. U.S. Pat. No. 4,334,534, issued to Ozaki, discloses an emergency airway tube for use in resuscitation of non-breathing patients by inserting the tube through the mouth until it randomly lodges either in the trachea or the esophagus. U.S. Pat. No. 4,584,998, issued to McGrail, discloses an endotracheal tube including up to three lumens, in addition to the primary lumen, which serves various functions to provide versatility in the treatment of patients. One lumen is used for inflating the cuff once the tube has been placed in the trachea; another is used to deliver oxygen or other gases by constant insufflation, intermittent jet ventilation or high frequency ventilation; and the third is used for monitoring and irrigation. U.S. Pat. No. 4,607,635, issued to Heyden, discloses an endotracheal tube with an elongated passage along its length. The tube has a plurality of ports along the passage to provide for removal of secretions that accumulate outside the tube and between the tube. U.S. Pat. No. 4,632,108, issued to Geil, discloses a flexible tubular assembly having a lumen for removing smoke generated during lazer surgery. U.S. Pat. No. 4,637,389, issued to Heyden, discloses a tracheal tube providing an expansible channel along its length, which normally maintains a generally concealed attitude within the trachael tube wall and adapts by expansion for the insertion of a suction catheter. U.S. Pat. No. 4,688,568, issued to Frass, discloses a tube that has an airway for sole esophageal obturator or endotracheal and esophageal-obturator ventilation and an inflatable cuff in the area of the tip of the airway and air-outlets in the area of the pharynx. U.S. Pat. No. 4,762,125, issued to Leiman, discloses a balloon-tipped suction catheter that embodies an elongated tube with a cannula extending along the elongated tube. U.S. Pat. No. 4,840,173, issued to Porter, III, discloses an endotracheal tube having dual passages provided by the merging of a ventilation tube and a suction tube. U.S. Pat. No. 5,520,175, issued to Fry, discloses an endotracheal tube with an inflatable cuff having a convex shaped superior surface forming a collection basin to facilitate accurate suctioning while tube is in position.

The above noted patent references fail to adequately address many important issues. Conventional endotracheal and tracheal tubes lack the ability to suction both oropharyngeal and gastroesophageal secretions, even when a patient is turned according to nationally instituted decubitus prevention protocols. They fail to provide a suction catheter or lumen that is replaceable while a patient is intubated. The prior art endotracheal tube designs do not adequately accommodate chlorhexidine rinses to prevent colonization of bacteria around the trachea area above the cuff and can trigger cough reflexes, which allow secretions and fluids to flow past the cuff. Conventional designs also fail to counter torquing of the cuff balloon that can occur when a patient coughs.

The patent references found fail to provide an endotracheal tube that adequately addresses the foregoing issues or that has a suction catheter or lumen that is replaceable while a patient is intubated, adapts to the contours of the tube and contains secretions even when a patient is turned. As the background devices fail to disclose an endotracheal tube and suction catheter system having these structural characteristics, the need for such a device is apparent. The instant invention addresses this by providing an endotracheal tube and suction catheter system comprising a replaceable suction/aspiration catheter, guide rail system and collection pocket that is designed to hold secretions even when a patient is turned.

BRIEF SUMMARY OF THE INVENTION

In light of the foregoing, it is an object of the present invention to provide an endotracheal tube that facilitates the convenient, safe removal of pooled secretions in the tracheal area above the cuff.

It is another object of the instant invention to provide an endotracheal tube having an aspiration or suction catheter that is replaceable, smooth and adapted for traversing an endotracheal tube for routine use of the suction catheter.

It is an additional object of the instant invention to provide an endotracheal tube system having a suction catheter that can be replaced while a patient is intubated with the endotracheal tube allowing for routine suction catheter changes.

It is a further object of the instant invention to provide an endotracheal tube and suction catheter system that facilitates the introduction of anti-microbial solutions into the tracheal area to kill bacterial colonizations.

It is also an object of the instant invention to provide an endotracheal tube and suction catheter system that can decrease the occurrence of aspiration/nosocomial pneumonia.

It is another object of the instant invention to provide an endotracheal tube and suction catheter system that can decrease the requirement for antibiotics.

It is still another object of the instant invention to provide an endotracheal tube and suction catheter system that can suction both oropharyngeal and gastroesophageal secretions, even when a patient is turned.

It is still an additional object of the instant invention to provide an endotracheal tube and suction catheter system that facilitates the use of chlorhexidine rinses to prevent colonization of bacteria around the trachea and cuff mating surfaces in a manner that alleviates aspiration secondary to the suction of fluids at the trachea cuff and avoids the triggering of the cough reflex as fluids migrate to the tracheal cuff.

It is still another object of the instant invention to provide an endotracheal tube and suction catheter system having a geometric design that counters the torque forces on the cuff when a patient coughs to keep the walls of the cuff against the trachea wall to prevent subglottic secretions from slipping past the cuff.

It is still a further object of the instant invention to provide an endotracheal tube and suction catheter system having a cuff with elongated sides to provide a greater surface area and less pressure per unit area on sensitive, delegate tracheal tissue to decrease the incidence of injuries associated with cuff pressure on the trachea.

It is yet another object of the instant invention to provide an endotracheal tube that is cost effective and adapted for existing manufacturing techniques.

In light of these and other objects, the instant invention comprises an endotracheal tube and suction catheter system having an inflatable cuff with a unique shape, collection pocket formed by the inflatable cuff and a unique railing system for controllably guiding a suction catheter along the tube and into or proximal to the pocket. The cuff and pocket facilitate the collection of pooled secretions that accumulate in the trachea area. Pooled secretions are collected in the cuff pocket and the cuff may be pitched toward the pocket or have a concave hemispherical design at the posterior pocket end and, or a convex hemispherical design at the anterior end to further urge pooled secretions into the pocket. The cuff preferably has an elongated parallelogram-like shape to counter the rocking phenomenon caused by a patient coughing or turning. The parallelogram-like shape causes the cuff to maintain its contact with the trachea walls so secretions and fluid do not leak past the cuff balloon. The suction catheter, which is guided along the tube toward the pocket, is used to aspirate the collected secretions in the pocket and above the cuff. The railing system allows the suction catheter to be replaced without having to remove the endotracheal tube. Although the instant invention is primarily described with reference to flexible endotracheal tubes, it may also be adapted for tracheal tubes, which are typically shorter and more rigid. The instant invention may also comprise a system having a suction catheter with a temperature probe and, or oropharyngeal system probe.

The endotracheal tube generally comprises a main lumen, cuff lumen, inflatable cuff with a tapered pocket and rail system designed for guiding a suction catheter along the main lumen. The rail system is found on the main lumen and suction catheter such that the catheter engages and slides along the main lumen to allow for the removal of pooled secretions. The rail system comprises a monorail that traverses the exterior surface of the main lumen and terminates at a predetermined distance above the cuff and pocket, and a corresponding bi-rail traversing the suction catheter. The suction catheter bi-rail slidably interlocks with the monorail and terminates at a stop defined by the distal end of the monorail. The monorail stop prevents the catheter from extending too far into the trachea and cuff pocket to protect the patient from trauma and the cuff from being punctured and to facilitate optimum placement of the suction catheter. The monorail stop is smooth and curved and tapers downward to the tube to prevent trauma to the patient's trachea during intubation. The bi-rail comprises two substantially parallel rails having a hooked contour along its interior surface that forms a channel for sliding over the monorail. The monorail comprises an elongated tongue having a cross-sectional shape, such as a mushroom-like shape or similar shape, that corresponds to the cross-sectional shape of the bi-rail groove. The bi-rail and tube provide walls of adherence for hardened, ossified secretions that inevitably develop during long term intubation. When removing the suction catheter the hardened secretions along the endotracheal tube, bi-rail, and in some instances the monorail, are removed. The bi-rail channel accommodates the application of a water-based lubricant, such as those sold under the trademark Surgilube, for decreasing friction as the catheter bi-rail is urged over the monorail. The bi-rail also provides increased stability for inserting the suction catheter. In an alternative embodiment, the cuff pocket and/or catheter section may comprise a radio opaque material or plastic that is detectable and viewable when inserted.

The cuff balloon comprises a cuff pocket for collecting pooled secretions. The cuff preferably has two interior pocket walls that form a tapered pocket when the cuff is inflated. The pocket walls may have a higher tensile strength to prevent the pocket from collapsing and to achieve the desired pocket shape. The superior anterior portion of the cuff may also extend outward at or near the top end in a manner that pitches toward the pocket or provides a hemispherical convex contour that facilitates migration of secretions into the tapered pocket. The cuff's posterior pocket end may also be pitched toward the pocket or have a concave, hemispherical design to further urge secretions into the pocket. The pocket preferably expands ninety to one-hundred and eighty degrees over the tube at its widest section and tapers into a point at the back of the pocket and a point at the top of the pocket. The point at the top of the pocket is preferably secured to the interior wall of the cuff and the point at the back of the pocket is secured to the tube proximal the bottom of the cuff. The pocket walls share common edges between the two points and each have a lower edge that is secured to main lumen. The lower edges are preferably ninety to one hundred and eighty degrees apart near the top of the pocket to achieve the proper width of the pocket. This retains collected secretions in the pocket and continues to facilitate the collection of secretions when the patient is turned. The pocket walls and cuff define an airtight interior volume that is inflated through the cuff lumen. The cuff lumen extends through the wall of the main tube and communicates with the inflatable cuff for selectively inflating and deflating the cuff with an external source of air, as is known in the art. When the cuff lumen is inflated it raises the top point and pocket walls until fully erect. When the cuff is deflated, the pocket collapses with the cuff. The design of the cuff and collection pocket urges the migration of secretions into the pocket, which retains the secretions even when a patient is turned. The cuff balloon may also be impregnated or coated with an anti-microbial solution that prevents the colonization of bacteria.

The main lumen comprises the main body of the invention. The main lumen is inserted into a patient's trachea for ventilation and/or anesthetic treatment of the patient's lungs. The cuff inflation lumen fluidly communicates with the cuff balloon for inflating and deflating the cuff.

To use the instant invention, a patient is intubated with the endotacheal tube. The tube may be fitted with the suction catheter at the time of intubation or thereafter. To mount the suction catheter on the tube, the bi-rail is aligned with and slidably inserted over the monorail so that the bi-rail wraps around the monorail. The suction catheter is urged down the tube until the bi-rail engages the monorail stop. When fully inserted, the suction catheter extends beyond the stop and into the cuff pocket. The same procedure is followed to insert a suction catheter while the patient is intubated. The suction catheter may be replaced without removing the endotracheal tube by sliding the suction catheter off the monorail and out of the patient's mouth and inserting a new catheter over the monorail as discussed. Once installed, an external vacuum source is used to aspirate secretions through the suction catheter.

In an alternative embodiment, the instant invention may comprise a tracheostomy tube instead of an endotracheal tube. The tracheostomy tube is merely a shorter, rigid version of the endotracheal tube of the instant invention and is inserted through the neck instead of through the mouth. Accordingly, the tracheostomy tube of the instant invention comprises all the elements of the endotracheal tube.

In accordance with these and other objects, which will become apparent hereinafter, the instant invention will now be described with particular reference to the accompanying drawings.

BRIEF DESCRIPTION OF THE SEVERAL VIEWS OF THE DRAWINGS

FIG. 1 is a front elevational view of the preferred embodiment of the endotracheal tube and suction catheter system of the instant invention illustrating the cuff deflated.

FIG. 2 is a front elevational view of the preferred embodiment of the endotracheal tube and suction catheter system of the instant invention illustrating the cuff inflated.

FIG. 3 is a front perspective partial enlarged view of the preferred embodiment of the endotracheal tube and suction catheter system of the instant invention illustrating the suction catheter installed and the monorail stop.

FIG. 5 is a cross sectional view of the preferred embodiment of the endotracheal tube and suction catheter system of the instant invention taken along cross section lines 5—5 of FIG. 2.

FIG. 6 is a cross sectional view of the preferred embodiment of the endotracheal tube and suction catheter system of the instant invention taken along cross section lines 6—6 of FIG. 2.

FIG. 7 is a cross sectional view of the preferred embodiment of the endotracheal tube and suction catheter system of the instant invention taken along cross section lines 7—7 of FIG. 2.

FIG. 10 is a cross sectional view of an preferred embodiment of the endotracheal tube and suction catheter system of the instant invention taken along cross section lines 6—6 of FIG. 2.

FIG. 12 is a front perspective view of another embodiment of the endotracheal tube and suction catheter system of the instant invention illustrating the pocket projecting from the tube, suction catheter and the monorail stop.

FIG. 13 is a cross sectional view of the embodiment of the endotracheal tube and suction catheter system of the instant invention shown in FIG. 12.

DETAILED DESCRIPTION OF THE INVENTION

With reference to the drawings, FIGS. 1–17 depict the preferred and alternative embodiments of the instant invention, which is generally referenced by numeric character 10 and, or as an endotracheal tube and suction catheter system 10.

Figure 9:
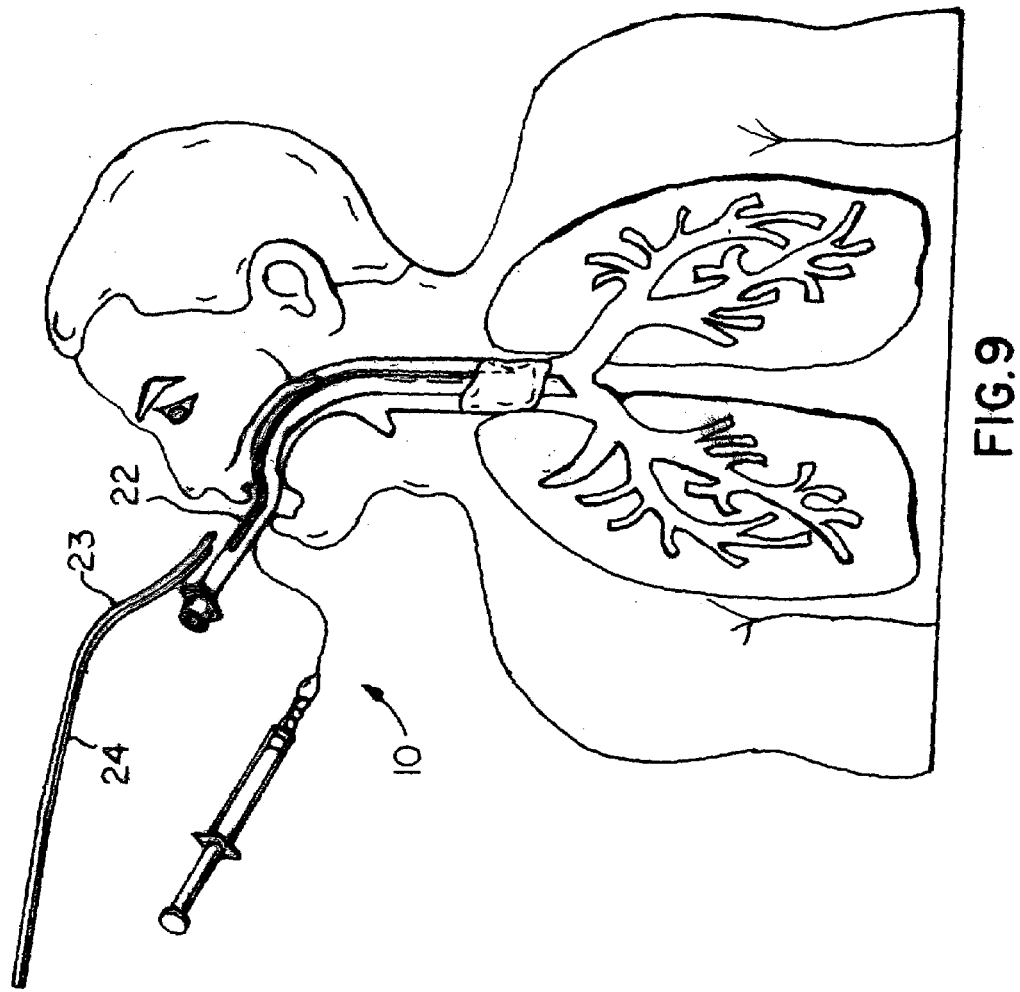
FIG. 9 is an illustration of the alternative embodiment of the endotracheal tube and suction catheter system of the instant invention in use.
Figure 8:
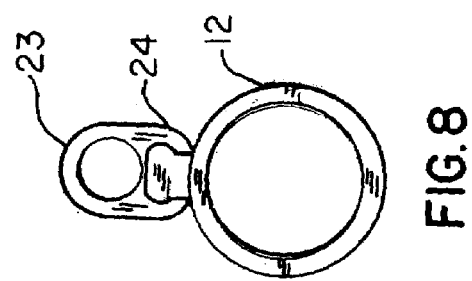
FIG. 8 is a cross sectional view of the preferred embodiment of the rail system and catheter of the instant invention.

With reference to FIGS. 1–5, the endotracheal tube and suction catheter system 10 generally comprises a main lumen 12 having an inflatable balloon cuff 14 with a collection pocket 30 for holding pooled secretions, suction catheter 23 for removing the pooled secretions and rail system 20 for guiding and positioning the suction catheter 23 in the vicinity of the collection pocket 30. The main lumen 12 comprises a conventional endotracheal tube having a central passageway 16, modified balloon cuff 14, inflation lumen 17 and Murphy eyelet 18. The inflatable cuff 14 is secured to the main lumen 12, as is known in the art, and defines the collection pocket 30 as shown in FIGS. 2–5. The balloon cuff 14 is preferably shaped substantially like a parallelogram to counteract torquing of the cuff 14 when the patient coughs. The torque force caused by coughing can cause the balloon cuff 14 to release away from trachea walls allowing the passage pneumonia causing secretions. Accordingly, one corner is raised higher than the other on at least one end. With reference to FIGS. 5 and 9, the extended, oblong anterior end 99 of the cuff 14 is preferably convex and faces the anterior or chest of the patient while the oblong corner on the posterior half of the cuff is preferably concave and faces the posterior of the patient. The other corner at the top end of the cuff 14 may also extend outward such that they form a hemispherical, concave surface while maintaining an overall parallelogram shape, as shown in FIG. 2. The shape of the cuff 14 at the top end urges the flow of secretions toward and into the cuff pocket 30 by utilizing gravity. The shape of the balloon cuff 14 also blocks the passage of secretions past the cuff 14. Conventional balloon cuffs can release away from the trachea walls when the patient coughs allowing pooled subglotic secretions to flow past the protective cuff shield increasing the risk of pneumonia. The parallelogram shaped cuff 14 of the instant invention provides greater surface area and is shaped in a manner that keeps the cuff 14 in contact with the tracheal walls even when a patient coughs. This prevents secretions from making it past the balloon cuff 14. The balloon cuff 14 also defines the collection pocket at a location in alignment with the suction end of the railing system 20 to insure proper positioning of the suction catheter 23.

The balloon cuff 14 defines the collection pocket 30, which receives pooled secretions. With reference to FIGS. 6, 7 and 10, the cuff pocket 30 preferably comprises a first pocket wall 31 and second pocket wall 33 secured inside the cuff volume. The pocket walls 31, 33 and cuff 14 form an airtight interior volume that is inflated through the cuff lumen 17. The first and second walls 31, 33 each have a lower edge 34, 36, respectively, that are secured to the exterior surface of the main lumen 12 within the pocket 30. The first and second walls 31, 33 have or share a common edge 32, which defines a top or forward connection point 42 and a rear connection point 44. The top connection point 42 is securely attached to or formed integrally with the interior surface of the balloon cuff 14 proximal the top, forward pocket edge 38. The rear connection point 44 is preferably secured to the main lumen 12 toward the back of the cuff 14. The first and second lower edges 34, 36, extend from the rear connection point 44 toward the forward pocket edge 38 preferably at a ninety-degree angle with respect to each other. At its widest point, the first and second lower edges 34, 36 are ninety to one hundred and eighty degrees apart. Accordingly, the lower edges 34, 36 form a triangle on the upper surface of the main lumen 12 at an angle that facilitates the collection of secretions even when a patient is turned. As the forward point 42 is attached to the cuff 14 and the rear point 44 is secured to the main lumen 12, the collection pocket 30 is formed when the cuff 14 is inflated. That is, the cuff 14 pulls the forward point 42 of the walls 31, 33 upward as the cuff 14 is inflated to form the pocket 30. The pocket walls 31, 33 may have a higher tensile strength to prevent the pocket 30 from collapsing under pressure when inflated and to achieve the desired pocket shape.

In an alternative embodiment, the pocket 30 may include first and second lower barriers 35, 37, which are joined to opposite sides of the main lumen 12 at one end, respectively, and to the walls 31, 33 at the other end, as shown in FIG. 10. Alternatively, the lower barriers 35, 37 may be attached to the interior of the balloon cuff 14, such that they extend between the main lumen 12 and cuff 14, as illustrated by the phantom lines in FIG. 10. The overall size and width of the collection pocket 30 is expanded by utilizing the lower barriers 35, 37 and expanded further by attaching the barriers 35, 37 to the cuff lining.

The cuff lumen 17 extends through the wall of the main tube 12 and communicates with the inflatable cuff 14 for selectively inflating and deflating the cuff 14 with an external source of air pressure, as is known in the art. When the cuff 14 is inflated it raises the top point 42 and pocket walls 31, 33 until the balloon cuff 14 is fully erect. When the cuff 14 is deflated, the pocket 30 collapses with the cuff 14. The design of the cuff 14 and collection pocket 30 urges the migration of secretions into the pocket 30, which retains the secretions even when a patient is turned.

Figure 4:
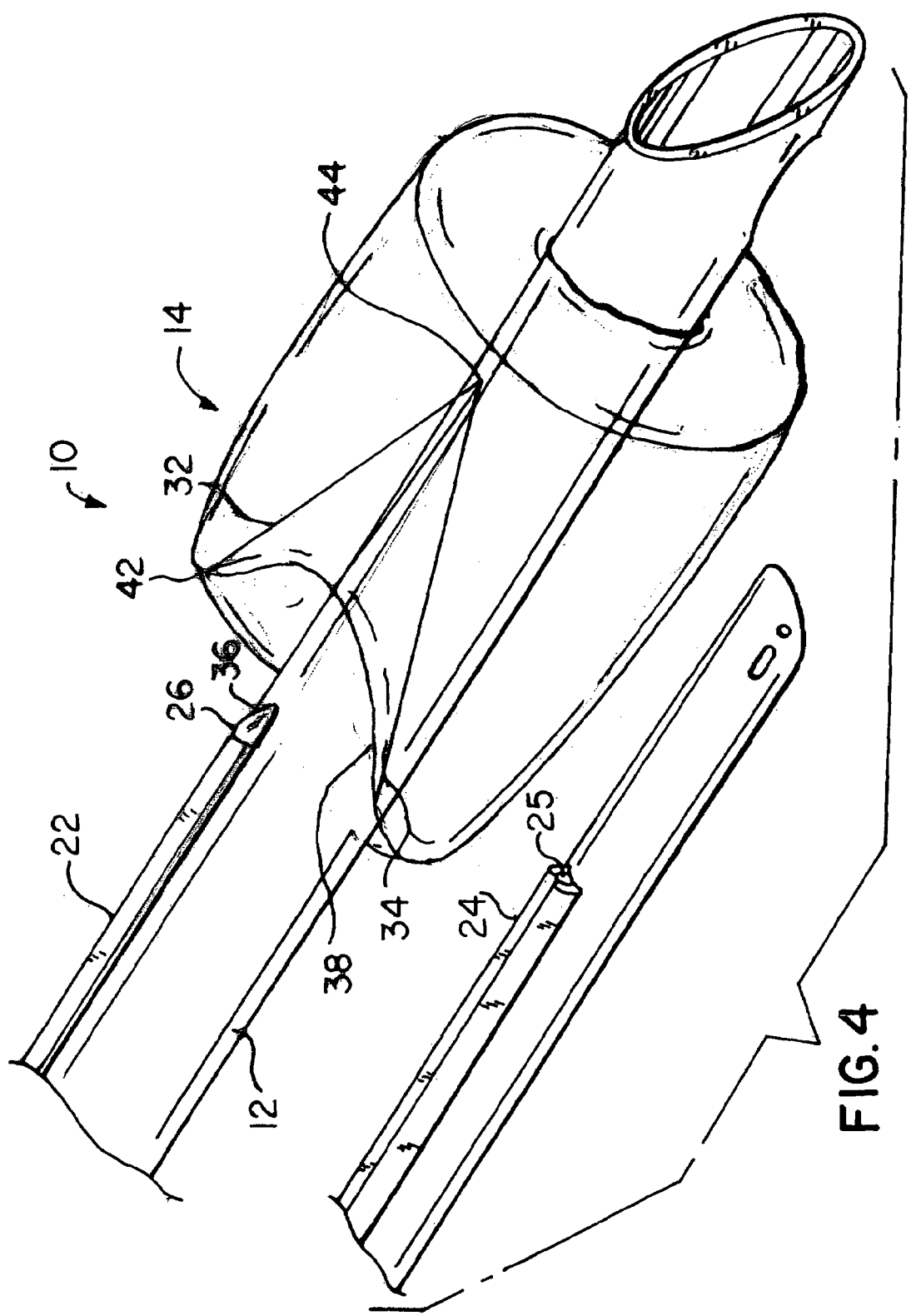
FIG. 4 is a front perspective partial and exploded view of the preferred embodiment of the endotracheal tube and suction catheter system of the instant invention illustrating the suction catheter prior to installation.

The instant invention further comprises a suction catheter 23 adapted for traversing the main lumen 12 and aspirating or suctioning secretions from the collection pocket 30. The suction catheter 23 is guided along the tube toward and in alignment with the pocket 30 by the rail system 20, as shown in FIGS. 3 and 4. The rail system 20 facilitates the removal and replacement of suction catheters 23 without necessitating the removal of the endotracheal tube 10. The rail system 20 is partially defined by the main lumen 12 and the suction catheter 23 such that the catheter 23 engages and slidably interlocks with corresponding railing for moving the catheter 23 along the main lumen 12. The rail system 20 comprises a monorail 22 and bi-rail 24. The monorail traverses the exterior surface of the main lumen 12 and terminates at a predetermined distance above the cuff 14 and pocket 30 and preferably in alignment with the top point 42 of the pocket 30. The bi-rail 24 traverses the suction catheter 23 and slidably engages the monorail. The monorail 22 and bi-rail 24 may comprise integral parts of the main lumen 12 and suction catheter 23, respectively.

With reference to FIG. 4, the monorail 22 comprises a T-stop 26, which is defined by the distal end of the monorail 22. The monorail stop 26 prevents the catheter from extending too far into the trachea and cuff pocket 30 to protect the patient from trachea trauma and to prevent puncturing the cuff 14. The stop 26 also insures optimum placement of the tip of the suction catheter 23 with respect to the pocket 30. The monorail stop 26 is smooth and curved and tapers down toward the tube 12 to prevent trauma to the patient's trachea during intubation. The monorail 22 is preferably shaped like a mushroom for slidably engaging the bi-rail 24 and has a low profile to limit or eliminate the risk of trachea trauma during intubation. The bi-rail 24 comprises two substantially parallel rails that form a corresponding mushroom-like channel 25 for sliding over the monorail 22. The monorail 22 and bi-rail channel 25 have corresponding cooperative cross-sectional shapes to facilitate secure, slidable movement of the catheter 23 along the monorail 22 and main lumen 12. The bi-rail channel 25 also provides a pocket for inserting a water-based lubricant, such as Surgilube, to reduce friction between the monorail 22 and bi-rail 24 when inserting the suction catheter 23. The bi-rail 24 also provides additional rigidity to the suction catheter 23 to facilitate the convenient placement and traversing of the suction catheter 23 over the main lumen 12. The bi-rail 24 and tube 12 provide walls of adherence for hardened, ossified secretions that inevitably develop during long term intubation and create a self-cleaning rail system when changing catheters 23. When removing the suction catheter 23 the hardened secretions are removed. The design of the rail system 20, suction catheter 23 and cuff 14 facilitate the application of cleansing and disinfecting rinses to prevent colonization of bacteria around balloon cuff 14 and trachea surfaces to reduce the risk of infections. The instant invention 10 also allows the application of antimocrobial or viscous Lidocaine rinses with no risk of aspiration when aspirating secretions and fluids from the cuff 14. The suction catheter 23 employed is preferably adaptable for use with a Lopez valve or comparable 3-way stopcocks for NGT/Dobbhoff tubes and allows for the administration of oral antimocrobial or viscous Lidocaine, chlorhexidine, gluconate and/or lido rinses via the suction catheter 23.

The monorail 22 and bi-rail 24 comprise unobtrusive, modest ridges designed to avoid snagging or causing trauma to the inner lining of throat during patient intubation. The monorail 22 and bi-rail 24 have rounded edges so they are unobtrusive. The rounded edges are smooth and continuous to reduce or prevent the incident of trauma to the inner lining of the patient's throat during intubation. The rounded edges of the monorail 22 have a convex mushroom design as noted above and the bi-rails 24 have corresponding mating contours that facilitate slidable engagement and disengagement between the monorail and bi-rail. The convex mushroom design also facilitates the easier removal of residue and hardened secretion build-ups.

In an alternative embodiment, the tube 10 may have strips 97 connected to the pocket 30 and main lumen 12, as shown in FIG. 3. The strips 97 control the height and opening of the pocket 30.

To use the instant invention, a patient is intubated with the endotacheal tube. The tube may be fitted with the suction catheter at the time of intubation or thereafter. To mount the suction catheter on the tube, the bi-rail is aligned with and slidably inserted over the monorail so that the bi-rail wraps around the monorail. The suction catheter is urged down the tube until the bi-rail engages the monorail stop. When fully inserted, the suction catheter extends beyond the stop and into the cuff pocket. The same procedure is followed to insert a suction catheter while the patient is intubated. The suction catheter may be replaced without removing the endotracheal tube by sliding the suction catheter off the monorail and out of the patient's mouth and inserting a new catheter over the monorail as discussed. Once installed, an external vacuum source is used to aspirate secretions through the suction catheter.

In one or more alternative embodiments, the instant invention 10 may comprise a suction catheter having one or more probes 28 disposed in the wall of the catheter 23 with or without a sensing tip 29 exposed. The probe 28 may comprise a temperature probe for monitoring a patient's temperature. The probe 28 may also comprise a oropharyngeal measurement system for early warning detection signals for tissue hypoperfusion, which may require an exposed tip 29. In another alternative embodiment, the endotracheal tube body 12 may comprise said probe(s) 28 in the wall as described above with respect to the catheter 23. In another alternative embodiment, the cuff balloon 14, and/or tube 12 surfaces may be impregnated, comprise or be coated with an anti-microbial solution for preventing the colonization of bacteria. In another alternative embodiment, the cuff pocket 30 and, or catheter 23, preferably proximal the tip, may comprise a radio-opaque material, such as in the form of plastic to facilitate viewing and gauging the tube 12, cuff pocket 30 and/or catheter 23 during use.

Figure 11:
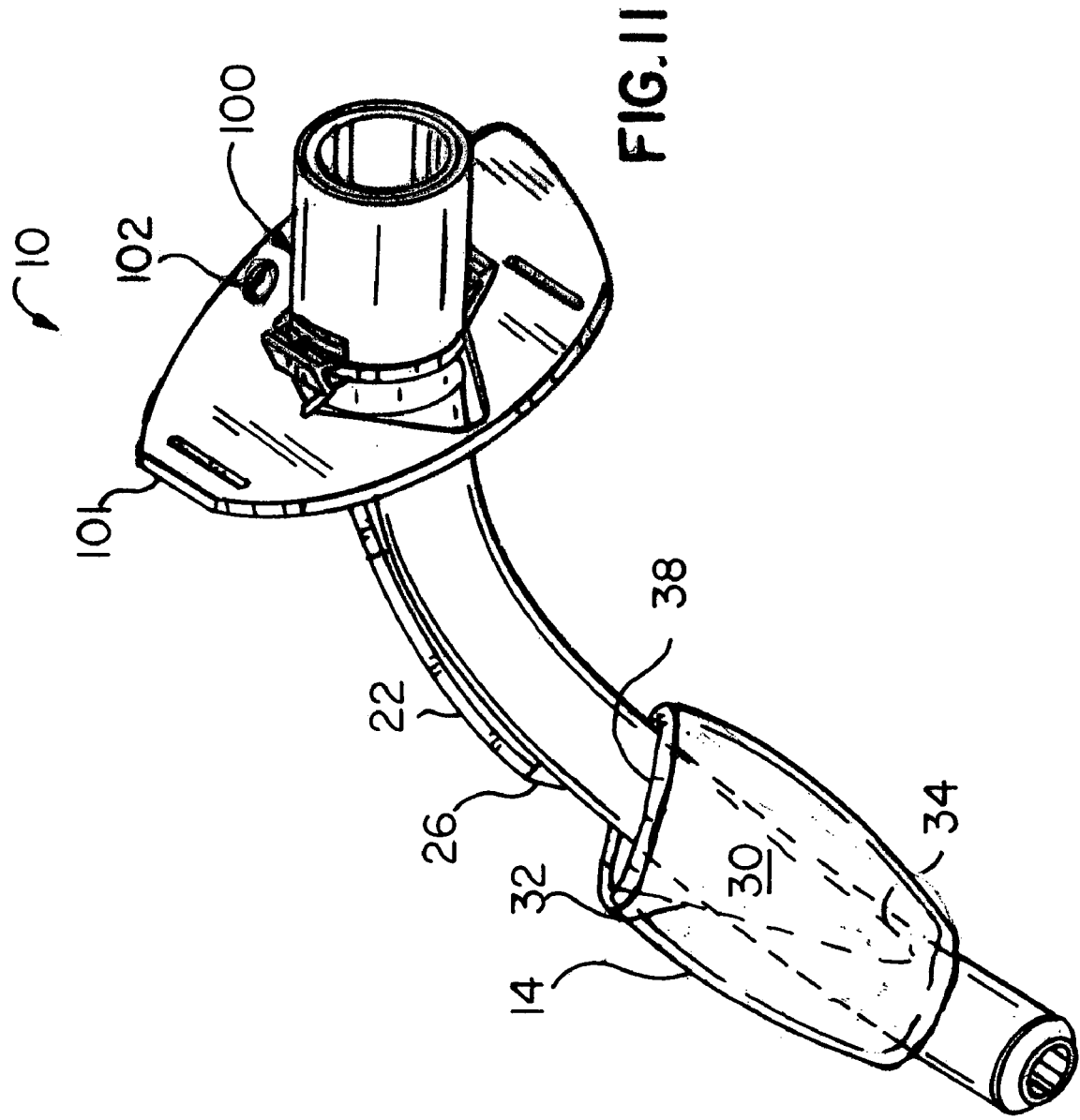
FIG. 11 is a perspective view of an alternative embodiment of the instant invention designed as a trachea tube.
Figure 14:
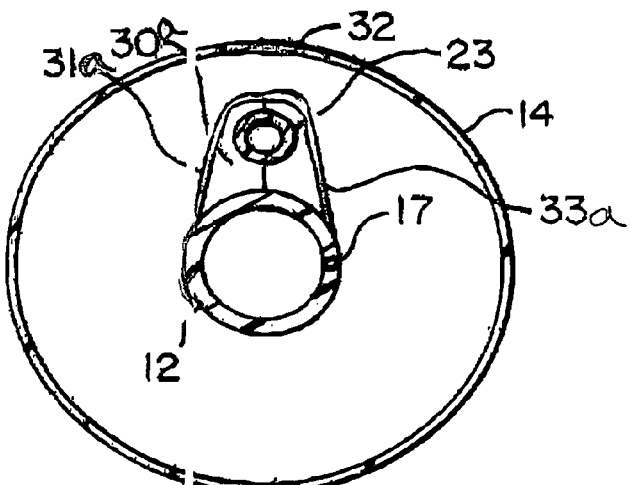
FIG. 14 is a cross sectional view of the preferred embodiment of the endotracheal tube and suction catheter system of the instant invention shown in FIG. 12.
Figure 15:
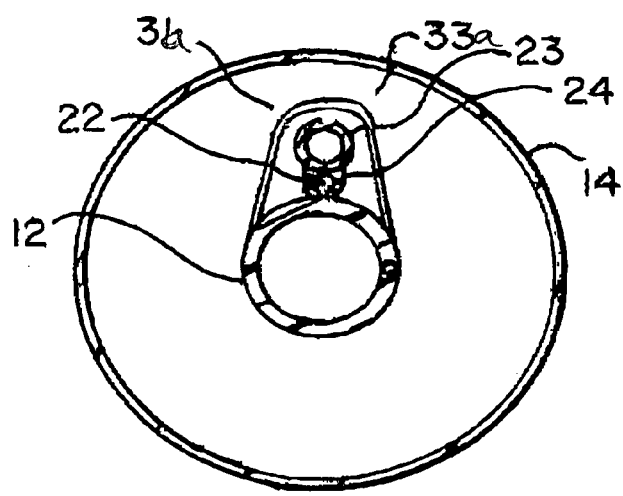
FIG. 15 is another cross sectional view of the preferred embodiment of the endotracheal tube and suction catheter system of the instant invention shown in FIG. 12.
Figure 16:
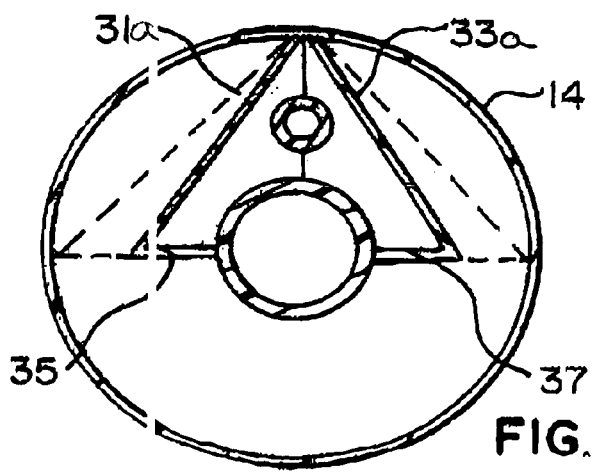
FIG. 16 is another cross sectional view of an alternative embodiment of the endotracheal tube and suction catheter system of the instant invention shown in FIG. 12.
Figure 17:
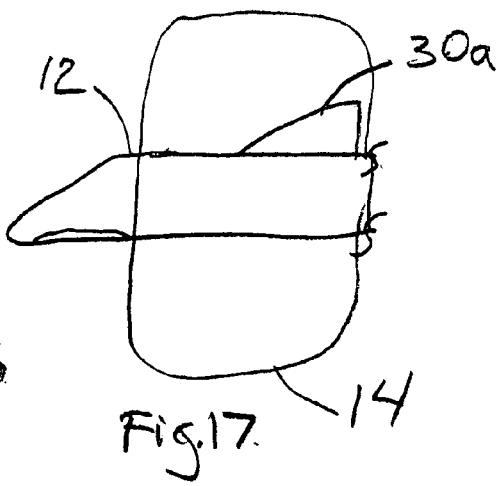
FIG. 17 is a side cross sectional elevational view of another embodiment of the collection pocket of the endotracheal tube and suction catheter system of the instant invention.

Although the invention 10 is primarily described as a flexible endotracheal tube, it may also comprise a rigid trachea tube having the same characteristics and attributes without departing from the scope and spirit of the instant invention as shown in FIG. 11. With reference to FIG. 11, the trachea tube 100 includes the rail system 22–25 and cuff balloon 14 having a tapered pocket 30, as described with reference to the endotracheal tube 10, but includes a trachea plate 101 having an aperture 102 for receiving and passing the suction catheter 23.

With reference to FIGS. 12–17, the instant invention 10 in another embodiment may comprise a collection pocket 30a defined by and/or extending outward from the main lumen 12 that does not collapse with the cuff 14 upon deflation. The alternative pocket 30a comprises one wall 31a, 33a that forms or a first wall 31a and second wall 33a that may blend together to form a unitary permanent wall structure that defines the collection pocket 30a and opening 98. The alternative pocket 30a preferably comprises the same or similar material as the main lumen 12 for convenient manufacture and use and that resists the pressure in the cuff 14 without collapsing that is exerted on the pocket 30a when the cuff 14 is inflated. The alternative pocket 30a may comprise a similarly rigid material that is capable of resisting pressure in the cuff 14 without significantly reducing the volume of the pocket 30a.

The instant invention has been shown and described herein in what is considered to be the most practical and preferred embodiment. It is recognized, however, that departures may be made therefrom within the scope of the invention and that obvious modifications will occur to a person skilled in the art.

The invention claimed is:

1. A tracheal secretion evacuation tube for removing pooled secretions from a patient's trachea area, said evacuation tube comprising:

a hollow tube having a wall defining a central passage along its longitudinal axis, said tube having a distal end and a proximal end wherein the distal end is inserted into the trachea area;

an inflatable cuff concentrically disposed on said tube proximal said distal end, said cuff having a top end, a bottom end and a cuff volume;

a tapered pocket positioned on said tube to receive descending secretions; said pocket comprising a cone-like shape defined by at least one wall between said cuff and said tube; said pocket tapering down into said cuff and only residing over a portion of the tube for facilitating the collection of descending secretions in the pocket at a plurality of angles;

inflation means for facilitating the selective inflation and deflation of said cuff; and means for guiding a suction catheter along said tube and at least proximal said pocket.

2. An evacuation tube as recited in claim 1, further comprising:

a suction catheter adapted for engaging said guiding means so as to facilitate the guidance of said catheter along said tube toward said cuff and into said pocket.

3. An evacuation tube as recited in claim 2, wherein said guiding means comprises:

a first track disposed along at least a portion of said tube above said cuff; and a second track disposed along at least a portion of said catheter, said first track and said second track being adapted for slidably interlocking to facilitate the guidance of said catheter above said first track and along said tube for at least partially entering said pocket without engaging said cuff and pocket walls.

4. An evacuation tube as recited in claim 2, wherein said catheter comprises at least one probe disposed in a wall of said catheter for reading the patient's temperature.

5. An evacuation tube as recited in claim 2, wherein said catheter comprises an oropharyngeal measurement device for monitoring tissue hypoperfusion.

6. An evacuation tube as recited in claim 2, wherein said catheter comprises a radio-opaque material for monitoring the location of said catheter from outside the patient's body.

7. An evacuation tube as recited in claim 3, wherein said device comprises means for introducing a lubricant through said first track.

8. An evacuation tube as recited in claim 3, wherein said device comprises means for introducing a lubricant through said second track.

9. An evacuation tube as recited in claim 1, wherein said cuff comprises:

an oblong parallelogram shape for maintaining contact of said cuff with the patient's trachea wall when the patient moves or coughs to prevent secretions from migrating past said cuff.

10. An evacuation tube as recited in claim 1, wherein said cuff comprises:

an upper leading edge above said pocket and lower recessed edge with respect to said upper leading edge below said pocket for counteracting torque forces caused when a patient coughs or turns to maintain contact of said cuff with the patient's trachea wall to prevent secretions from migrating past said cuff.

11. An evacuation tube as recited in claim 1, wherein said pocket wall comprises a material having a higher tensile strength then said cuff to prevent said pocket from collapsing when inflated or deflated.

* * * * *